(12) United States Patent
Yu et al.

(10) Patent No.: US 8,014,494 B2
(45) Date of Patent: Sep. 6, 2011

(54) SINGLE-ARC DOSE PAINTING FOR PRECISION RADIATION THERAPY

(75) Inventors: Cedric X. Yu, Clarksville, MD (US); Shuang Luan, Albuquerque, NM (US); Danny Z. Chen, Granger, IN (US); Matthew A. Earl, Crownsville, MD (US); Chao Wang, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 128 days.

(21) Appl. No.: 12/589,205

(22) Filed: Oct. 20, 2009

(65) Prior Publication Data

US 2011/0091015 A1    Apr. 21, 2011

(51) Int. Cl.
*A61N 5/10* (2006.01)
*G21K 1/02* (2006.01)
*H05G 1/42* (2006.01)

(52) U.S. Cl. .............................. 378/65; 378/148; 378/97
(58) Field of Classification Search .................. 378/62, 378/64, 65, 91, 95, 97, 108, 145, 147–153
See application file for complete search history.

(56) References Cited

U.S. PATENT DOCUMENTS

| | | | | |
|---|---|---|---|---|
| 6,757,355 | B1 * | 6/2004 | Siochi | 378/65 |
| 6,907,105 | B2 * | 6/2005 | Otto | 378/65 |
| 2009/0207975 | A1 * | 8/2009 | Bourne | 378/150 |
| 2009/0213991 | A1 * | 8/2009 | Brown et al. | 378/65 |
| 2009/0220046 | A1 * | 9/2009 | Ji et al. | 378/65 |
| 2010/0054410 | A1 * | 3/2010 | Nord et al. | 378/65 |

* cited by examiner

*Primary Examiner* — Irakli Kiknadze
(74) *Attorney, Agent, or Firm* — Benjamin Aaron Adler

(57) ABSTRACT

Provided herein are methods and systems for designing a radiation treatment for a subject using single arc dose painting. The methods and systems comprise an algorithm or a computer-readable product having the same, to plan the radiation treatment. The algorithm converts pairs of multiple leaf collimation (MLC) leaves to sets of leaf aperture sequences that form a shortest path single arc thereof where the pairs of MLC leaves each aligned to an intensity profile of densely-spaced radiation beams, and connects each single arc of leaf apertures to form a final treatment single arc. Also provided is a method for irradiating a tumor in a subject using single arc dose painting.

20 Claims, 11 Drawing Sheets

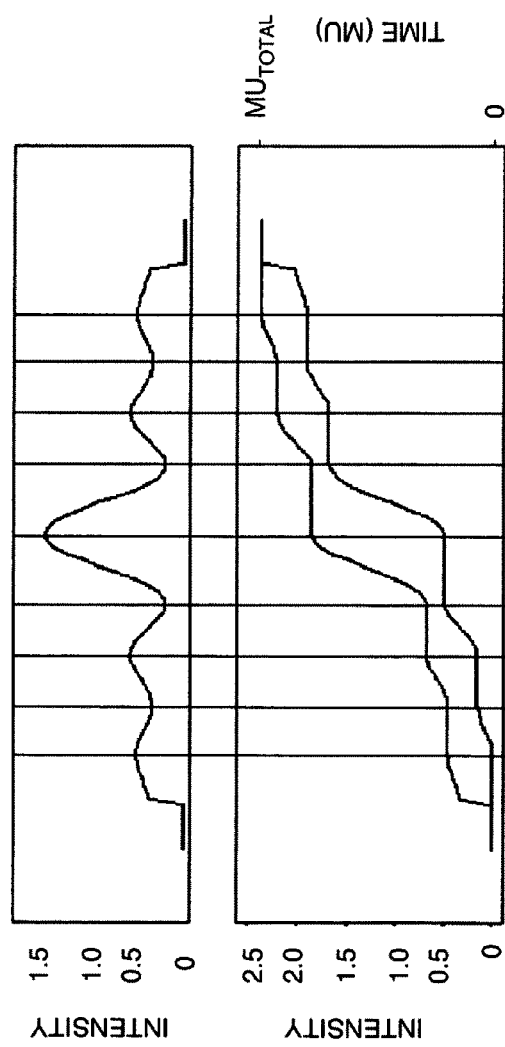
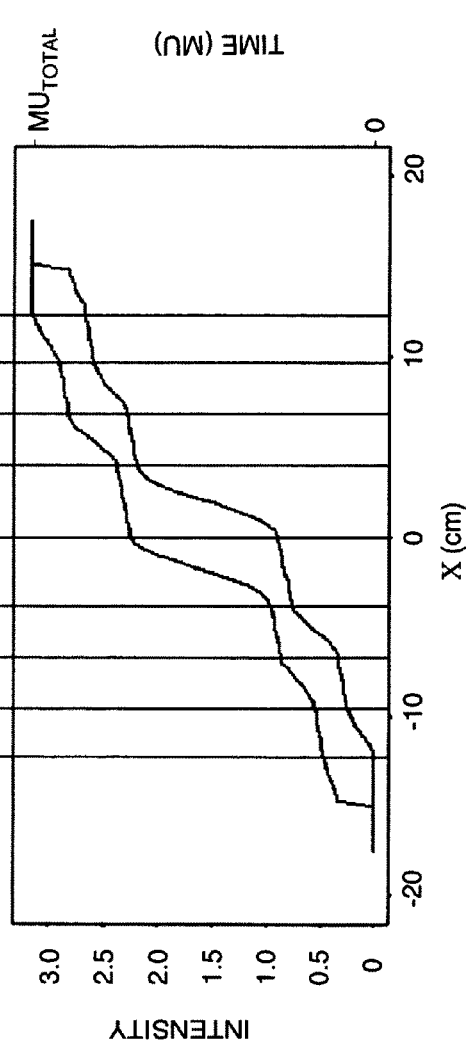
Fig. 4A
Fig. 4B
Fig. 4C

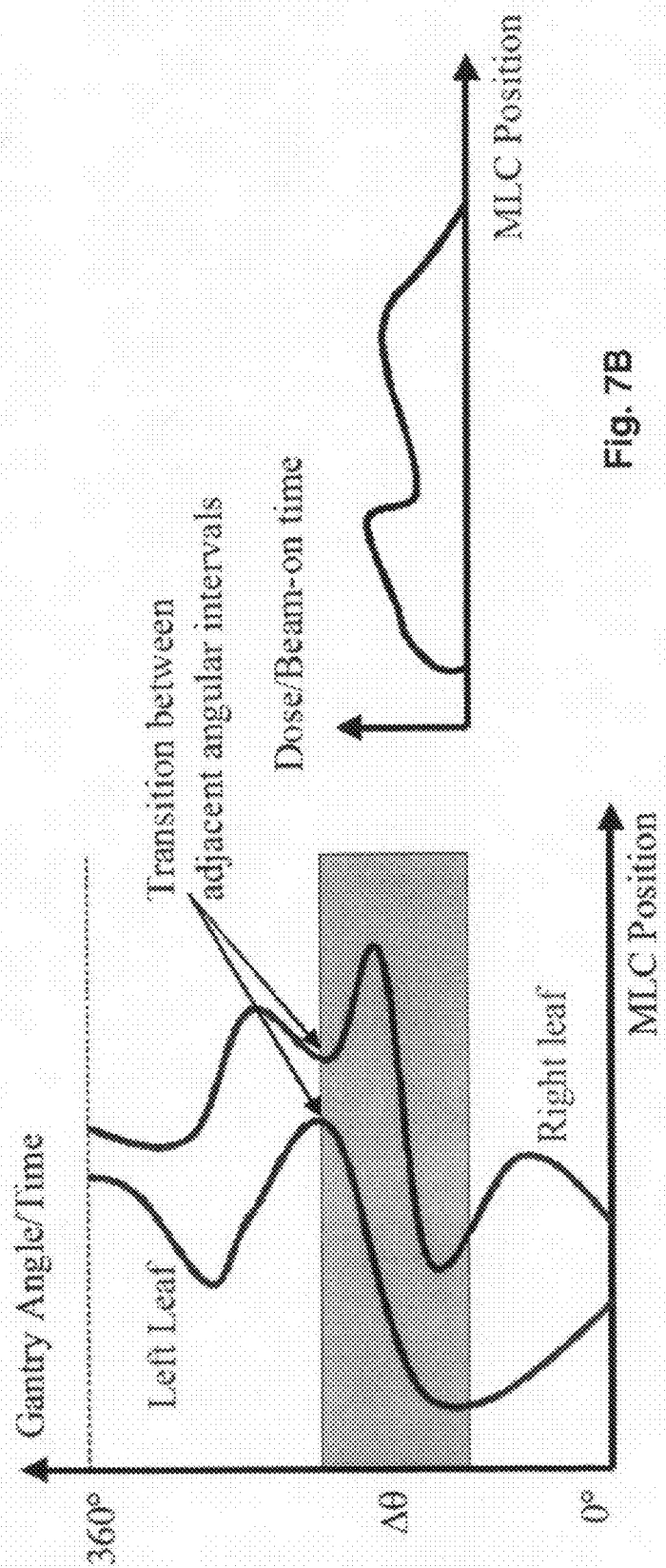

SINGLE-ARC DOSE PAINTING FOR PRECISION RADIATION THERAPY

FEDERAL FUNDING LEGEND

This work was supported by National Science Foundation Grant No. CCF-0515203 and by National Institutes of Health Grant No. CA117997. The U.S. Government has certain rights in this invention.

CROSS-REFERENCE TO RELATED APPLICATIONS

This U.S. national application claims benefit of priority under 35 U.S.C. §120 of international application PCT/US2008/005028, filed Apr. 18, 2008 which claims benefit of priority under 35 U.S.C. §119(e) of provisional application U.S. Ser. No. 61/913,175, filed Apr. 20, 2007, now abandoned.

BACKGROUND OF THE INVENTION

1. Field of the Invention

The present invention relates to the field of radiation oncology for malignant tumors and the like. Specifically, the present invention provides methods and systems for planning delivery of radiation therapy by means of a single-arc dose of radiation.

2. Description of the Related Art

Conformal radiation therapy is an important procedure available to the physician for the treatment of malignant tumors. Such therapy is used for eradicating or shrinking tumors that are relatively inaccessible to other modes of treatment such as surgical excision. However, because the ionizing radiation that is administered is damaging to both healthy and malignant tissue, it is important to confine the effect of the irradiation to the target tissue, to the extent possible, while sparing the adjacent tissue by minimizing irradiation thereto. To achieve this goal, various techniques of irradiating a target tumor with a defined beam of ionizing radiation have been devised.

Although simple masking techniques using radiation absorbing materials have some utility, techniques using radiation beams directed at the target tissue from various angles about a patient have come to be preferred. Such beams are often provided from a radiation source, e.g., x-ray photons or high-energy electrons, mounted on a rotating gantry, so that the radiation source revolves in a generally circular path while providing a beam of radiation directed generally at the isocenter of such a path. A patient is positioned within the circular path, preferably with the tumor located, to the extent possible, at the isocenter for receiving the maximum dose of radiation as the source is revolved. The cross-sectional shape and size of the radiation beam is typically varied as the source is positioned at different angles by rotation of the gantry in order to assure, to the extent possible, that the radiation is incident on the tumor itself and not on adjacent healthy tissue.

A number of techniques have been developed with the intention of providing for maximum absorption of radiation within the tumor while minimizing exposure of adjacent healthy tissue. Intensity-modulated radiation therapy (IMRT) was developed based on the principle that for a given tumor, there is a set of preferred ways to direct the radiation to it. More radiation can be sent through some beam angles than others and within the same beam angle, there are preferred locations through which the radiation is directed to the tumor. Computer-assisted treatment planning systems have been developed to take advantage of such preferred angles and locations, e.g., by varying the intensity of the radiation beam across the radiation fields, in order to accomplish better treatment regimens.

Consequently, intensity-modulated radiation therapy (IMRT) has been widely adopted as a new tool in radiation therapy to deliver high doses of radiation to the tumor while providing maximal sparing of surrounding critical structures. Both rotational and gantry-fixed IMRT techniques have been implemented clinically using dynamic multileaf collimation (DMLC) (1-6).

In gantry-fixed IMRT, multiple radiation beams at different orientations, each with spatially modulated beam intensities, are used (1-2, 4). The beams may be administered to the patient in a single transverse plane as the source revolves around the patient (coplanar) or may be shifted axially with respect to the patient (non-coplanar). Rotational IMRT, typically, administered by a continuously revolving source that is also moved axially along the patient, as it is currently practiced, mainly employs temporally modulated fan beams (3). Although the quality of IMRT treatment plans has steadily improved, the plans tend to be relatively complicated, which makes for a somewhat inefficient delivery of treatment. Consequently, labor-intensiveness has been one of the drawbacks of IMRT. Furthermore, in general, a large number of different complex field shapes is often needed, which also compromises the efficiency of the treatment and can result in an increased number of collimator artifacts (7). Nevertheless, while long-term clinical results of IMRT treatments are still limited, initial results appear very promising, and with increased use of IMRT, more encouraging results are emerging.

U.S. Pat. No. 5,818,902 to Yu teaches the use of overlapping multiple arcs to deliver modulated beam intensities around the patient which is called intensity-modulated arc therapy (IMAT). Delivery of the radiation during overlapping multiple arcs achieves modulated beam intensities at all angles around the patient (5-6). However, IMAT has not been widely adopted for clinical use. In IMAT, the intensity distributions are first optimized using a treatment planning system for tightly-spaced beam angles every 5-10 degrees all around the tumor. These intensity distributions are then approximated by a stack of uniform intensity segments with different cross sectional shapes. These stacks of uniform beam segments at all beam angles are then sequentially administered as the radiation source describes multiple rotational arcs while the beam cross sections are defined at each angular position by a multi-leaf collimator (MLC) with its leaves moved by a computer-programmed controller to provide a sequence of predetermined apertures.

The inverse planning procedures used to determine beam cross-sections and intensities when planning IMRT and IMAT treatments have typically required the user to predetermine the number of beams to use and their orientations. This limitation can significantly affect the quality of the treatment plans because the most preferred angle might be completely missed. Rotational IMRT does not have such problems since all angles are considered in the plan.

Furthermore, because the delivery of IMAT requires the use of multiple (4-11) arcs, each of which may take 1 to 2 minutes to deliver, the total treatment time is similar to that of fixed beam IMRT treatments. It is also relevant that, even when intensity distribution is determined for densely-spaced beam angles, i.e., 5 to 10 degrees, and sequenced for delivery in a limited number of multiple arcs, the resultant distribution of radiation absorption in the tumor can still only approximate that which would be provided by optimized beam intensities and cross-sections, because each of the planned beams may require significant variations that cannot be accommodated by the plan as executed by the equipment. As a result, the final IMAT plan is almost always degraded from the unconstrained optimized plan.

One attempt to solve this problem is a method for optimizing IMAT using Direct Aperture Optimization, in which the shape and weight of the apertures contained in one or more arcs are optimized simultaneously (8). A similar method (9), who showed that a single arc optimization using a method similar to Direct Aperture Optimization could generate satisfactory treatment plans for a simple case. In both methods, a limited number of beam angles were used to illustrate the principle. For complicated cases, single-arc optimization over a limited number of angles cannot generate plans that rival fixed-beam IMRT plans (8). Using such methods, it is prohibitive with today's technology to optimize the rotational delivery with more beam angles, because pencil beams must be calculated for all the beam angles (8-9).

Another concern with current radiation treatment planning methods is that no method developed hitherto can create a rotational IMRT plan that consistently rivals fixed beam IMRT without requiring beam intensity modulation. For simple cases it was demonstrated that a single optimized arc can yield results as good as those of fixed-field IMRT, while, for more complicated cases, such as head and neck cases with multiple targets, such an approach would not work well, and intensity modulation is required (8). Although allowing the planned dose rate to vary with gantry angle provides a new degree of freedom, such relaxation of a restraint is not sufficient in itself to establish that a single arc using the described optimization method can replace multiple-arc IMAT. Treatment planning using current optimization schemes requires intensity modulation consistently to rival fixed beam IMRT (10). Another method that can achieve very good efficiency utilizes optimization based on the direct aperture optimization method of Shepard et al (10). However, although the optimization starts with a limited number of fields and the connectedness of the field shapes can be ignored, as the optimization progresses, constraint to force the shape-connectedness will compromise the quality of he treatment plans. As the result, one would know what the ultimate plan quality is like.

Thus, there is a recognized need in the art for improved radiation therapy planning methods that enable greater efficiency in delivery of radiation therapy. More specifically, the prior art is deficient in methods and systems for single-arc dose radiation therapy. The present invention fulfills this long-standing need and desire in the art.

SUMMARY OF THE INVENTION

The present invention is directed to a method for designing a radiation treatment for a subject using single arc dose painting. The method comprises providing an unconstrained optimization map which supplies intensity profiles of densely-spaced radiation beams and aligning each intensity profile to a pair of multiple leaf collimation (MLC) leaves. A shortest path algorithm is applied to convert each pair of MLC leaves to a set of leaf aperture sequences, where each set of leaf aperture sequences forms a shortest path single arc thereof and each single arc of leaf apertures is connected to form a final treatment single arc, thereby designing the single arc dose painting radiation treatment. The present invention is directed to a related method further comprising delivering a continuous dose of radiation to the subject through each aperture during a single rotation along one or more final treatment single arc paths. The present invention is directed to another related method further comprising adjusting a shape of the aperture as a radiation dose delivery angle changes along the final treatment single arc. The present invention is directed to yet another related method for irradiating a tumor in a subject with the continuous dose of radiation through sets of multiple leaf collimation (MLC) aperture sequences during a single rotation along one or more of the treatment single arc paths. The present invention is directed a related method further comprising adjusting the aperture shape as described supra. Further still to these related methods the present invention is directed to a method further comprising repeating the irradiation step during another rotation along the treatment single arc path(s).

The present invention is directed further to a system for delivering radiation treatment using single arc dose painting. The system comprises a radiation source for generating a radiation beam, a multiple leaf collimator having a plurality of leafs for shaping the radiation beam, a structure for generating an unconstrained optimization map of intensity profiles of densely-spaced radiation beams, a structure for aligning each intensity profile to a pair of multiple leaf collimation (MLC) leaves, and a structure for applying a shortest path algorithm, said shortest path algorithm converting each pair of MLC leaves to a set of leaf aperture sequences forming a shortest path single arc thereof, such that the shortest path algorithm further connects each single arc of leaf apertures to form a final treatment single arc effective for single arc dose painting. The present invention is directed a related system where the shortest path algorithm further comprises adjusting the aperture shape as described supra.

The present invention is directed further still to a computer-readable medium tangibly storing an algorithm to determine a final single arc path for a single arc dose painting radiation treatment. The algorithm enables instructions to convert pairs of multiple leaf collimation (MLC) leaves to sets of leaf aperture sequences that form a shortest path single arc thereof, where the pairs of MLC leaves each are aligned to an intensity profile of densely-spaced radiation beams, and to connect each single arc of leaf apertures to form a final treatment single arc. The present invention is directed a related computer-readable medium where the shortest path algorithm further enables adjusting the aperture shape as described supra.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims.

The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE DRAWINGS

FIGS. 4A-4B illustrates sliding window leaf sequencing. In FIG. 4A the desired intensity profile is aligned with a leaf pair. FIG. 4B shows separated intensity profiles to be conformed by the leading (right) and training (left) leaves. FIG. 4C shows adjusted leaf traveling trajectories after considering the physical constraints of leaf travel.

FIGS. 7A-7B illustrate the planning of a single arc dose painting.

DETAILED DESCRIPTION OF THE INVENTION

I. Definitions

Figure 1A:
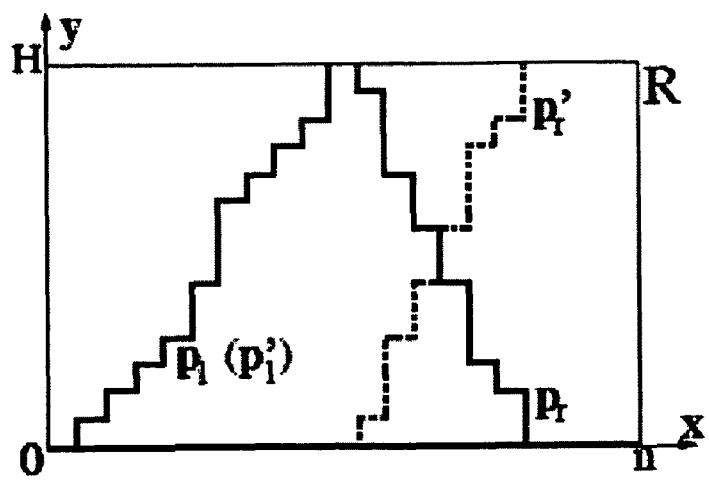
FIGS. 1A-1C illustrate how to flip the monotone decreasing path $p_r$ to a monotone increasing path $p'_r$ (FIG. 1A), how to flip two monotone decreasing paths $p_l$ and $p_r$ to two monotone increasing paths $p'_l$ and $p'_r$ (FIG. 1B) and how the xy-monotone region enclosed by the two paths $p'_l$ and $p'_r$ in FIG. 1B corresponds to a sequence of n vertical bars $B_1 B_2, \ldots, B_n$ (FIG. 1C). Note that after the flipping operations in FIGS. 1A-1B, neither the steepness nor the closeness constraint is violated, and $I_{i,pl,pr} = I_{i,p'l,p'r}$ holds for every i, which implies that the total error remains the same.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "about" refers to numeric values, including whole numbers, fractions, percentages, etc., whether or not explicitly indicated. The term "about" generally refers to a range of numerical values, e.g., +/−5-10% of the recited value, that one would consider equivalent to the recited value, e.g., having the same function or result. In some instances, the term "about" may include numerical values that are rounded to the nearest significant figure.

As used herein, the term "subject" refers to any recipient of single arc dose painting radiation treatment

II. Present Invention

In one embodiment of the present invention there is provided method for designing a radiation treatment for a subject using single arc dose painting, comprising providing an unconstrained optimization map which supplies intensity profiles of densely-spaced radiation beams; aligning each intensity profile to a pair of multiple leaf collimation (MLC) leaves; applying a shortest path algorithm to convert each pair of MLC leaves to a set of leaf aperture sequences, where the set of leaf aperture sequences form a shortest path single arc thereof; and connecting each single arc of leaf apertures to form a final treatment single arc, thereby designing the single arc dose painting radiation treatment.

Further to this embodiment the method comprises delivering a continuous dose of radiation to the subject through each aperture during a single rotation along one or more final treatment single arc paths. In another further embodiment the method comprises adjusting a shape of the aperture as a radiation dose delivery angle changes along the final treatment single arc.

In all embodiments the paths of more than one single arc may be non-coplanar. Also, the apertures may sweep back and forth along the single arc path during delivery of the radiation dose. In addition multiple leaf collimation may be dynamic.

In all embodiments sequencing leaf apertures may comprise one or more of a line segment approximation on component intensity profiles leaf position, weight optimization of apertures or optimization of leaf position and aperture weight. Also, the leaf aperture sequences in each set may have one or both of a different starting or ending leaf aperture. In addition, starting and ending positions of a leaf aperture trajectory may be fixed.

In another further embodiment of the present invention there is provided a method irradiating a tumor in a subject with the continuous dose of radiation through sets of multiple leaf collimation (MLC) aperture sequences during a single rotation along one or more of the treatment single arc paths. Further still to this further embodiment the method may comprise adjusting a shape of the aperture as a radiation dose delivery angle changes along the treatment single arc to keep the dose constant. Further still to both of these further embodiments the method may comprise repeating the irradiation step during another rotation along the treatment single arc path(s).

In another embodiment of the present invention there is provided a system for delivering radiation treatment using single arc dose painting, comprising a radiation source for generating a radiation beam; a multiple leaf collimator having a plurality of leafs for shaping the radiation beam; a structure for generating an unconstrained optimization map of intensity profiles of densely-spaced radiation beams; a structure for aligning each intensity profile to a pair of multiple leaf collimation (MLC) leaves; and a structure for applying a shortest path algorithm, where the shortest path algorithm converts each pair of MLC leaves to a set of leaf aperture sequences forming a shortest path single arc thereof and where the shortest path algorithm further connects each single arc of leaf apertures to form a final treatment single arc effective for single arc dose painting.

Further to this embodiment the shortest path algorithm may adjust a shape of the leaf aperture as a radiation dose delivery angle changes along the final treatment single arc.

Also the shortest path algorithm may sequence leaf apertures via one or more of a line segment approximation on component intensity profiles leaf position, weight optimization of apertures or optimization of leaf position and aperture weight. In addition multiple leaf collimation may be dynamic.

In yet another embodiment of the present invention there is provided a computer-readable medium tangibly storing an algorithm to determine a final single arc path for a single arc dose painting radiation treatment, said algorithm enabling processor-executable instructions to convert pairs of multiple leaf collimation (MLC) leaves to sets of leaf aperture sequences that form a shortest path single arc thereof, where the pairs of MLC leaves are each aligned to an intensity profile of densely-spaced radiation beams; and connect each single arc of leaf apertures to form a final treatment single arc. Further to this embodiment the algorithm may enable instructions to adjust a shape of the leaf aperture as a radiation dose delivery angle changes along the final treatment single arc thereby keeping the dose constant. Also, the algorithm may sequence leaf apertures via one or more of a line segment approximation on component intensity profiles leaf position, weight optimization of apertures or optimization of leaf position and aperture weight.

Provided herein are methods and systems to plan and deliver a new rotational radiation therapy, identified herein as single arc dose painting (SADP), that can achieve a quality of treatment comparable to that of multi-arc IMAT using only one continuous rotation of the beam around the patient. The efficiency of such treatment delivery, as compared with that of IMAT, is significantly improved. Generally, the difference in the methods provided herein from prior methods is that the planning process is two steps. In the first step, intensity distributions are optimized over densely spaced beams, for example, on 36 or 72 fields. Because no delivery constraints are applied at the optimization step, the plan quality represents the ultimate. In the second step, the intensity modulated beams are sequenced into a single arc delivery, Planning a single arc capable of delivering the ultimately optimal radiation treatment is based on the recognition that the same intended dose to the tumor delivered by an aperture at a planned angle can be delivered by a slightly modified aperture from a slightly different angle. Consequently, a single rotation with dynamically varying apertures can achieve the same results as a procedure that delivers a plurality of intensity modulated fixed beams.

Furthermore, methods to convert the intensity or fluence patterns in the target, as optimized at fixed beam angles, into a single arc of beam rotation are also new and innovative. The inventive leaf sequencing method of the invention achieves an interconnected relationship of multiple leaf collimator (MLC) apertures so that the MLC leaves are not required to move large distances between adjacent angles of the planned treatment. By sweeping the apertures (windows) back and forth, the requirement of connectedness is much easier to meet.

Also, the dose rate can change among the angular intervals. However, such a change in dose rate is not a requirement. Typically, the aperture size and shape can be optimized to maintain a substantially constant dose rate throughout the entire treatment arc.

Within a planning interval, the apertures can have different weights, delivered either through dose rate variation with all apertures occupying the same angular range or delivered without dose rate variation by allowing the aperture with higher weights to be delivered over a larger angular range. That is, the method is applicable to machines with and without the ability to change dose rates during delivery.

For treatment of tumor or other sites amenable to radiation therapy where use of multiple non-coplanar arcs is beneficial, multiple non-coplanar arcs can be planned according to the methods of the invention. However, with single arc dose painting, it is typically unnecessary to have overlapping arcs. Accordingly, the dose overlap in the tumor is considered, rather than beam overlap in each beam direction as with current IMRT planning. This relies on the recognition that the same dose can be delivered to the tumor by two beam apertures of slightly different shapes directed at the tumor from two angular directions a few degrees apart.

Planning starts with an unconstrained optimization with a large number of beams evenly spaced, for example, every 5-10 degrees. Depending on the complexity of the optimal intensity distribution, different number of apertures and weights are initialized using a "sliding window" line-segment approximation. Because the initial shapes are derived from the "sliding window" principle, the apertures are interconnected. The shape and weights of these apertures are further optimized (fine-tuned) to improve the plan quality. To deliver these apertures in one arc, they are spaced within their own planning angular interval by moving the overlapping apertures to other beam angles within the interval. To ensure that the apertures deliver the same dose to the tumor as they are moved away from the planned angle, the aperture shapes are varied, depending on how many degrees they are moved from the planned angle. Adjusting the aperture shape is to faithfully create the intensity maps that were created under unconstrained optimization and to maintain the ultimate plan quality.

Intensity modulation is allowed during intensity optimization and more than one aperture shapes is allowed within each planning angular interval. As compared with IMAT, the apertures are spaced and adjusted within the planning angular interval rather than overlapped to be delivered by using multiple arcs. Because, as described herein, an entire treatment dose is delivered in a single rotation, the number of different apertures per planning angular interval can vary according to the complexity of the required intensity distribution.

As such, systems effective to deliver radiation to a tumor using single arc dose painting comprise those radiation delivery devices having suitable structures for radiation therapy of malignant tumors or other conditions responsive to such treatment. As is known in the art such devices comprise at least a source of radiation, amoveable, rotatable gantry, a multiple leaf collimator, e.g., a dynamic multiple leaf collimater, a platform for a subject receiving radiation therapy, and the necessary computer hardware and software, processor, memory and network or other connections necessary to run the device. In addition, the system comprises a module or structure, such as, but not limited to, a computer memory, a computer-readable memory or computer program to, storage device which is suitable to tangibly store and execute the algorithms described herein, such as, standard algorithms for intensity profile optimization and the novel short path algorithms provided herein.

The following examples are given for the purpose of illustrating various embodiments of the invention and are not meant to limit the present invention in any fashion.

EXAMPLE 1

Constrained Coupled Path Planning (CCPP)

In constrained coupled path planning, the starting and ending points of the sought paths are prespecified. Precisely, the constrained coupled path planning (CCPP) problem is: Given an n×H uniform grid $R_g$, a non-negative function $f$ defined on the integers in $\{1, 2, \ldots, n\}$, and positive integers $l_{start}$, $r_{start}$, $l_{end}$, $r_{end}$, c, and $\Delta$ ($\Delta \leq H$), find two noncrossing paths $p_l$ and $p_r$ of height H along the edges of $R_g$ to minimize the total error $\epsilon(p_l, p_r) \Delta = \Sigma_{i+1}^n |l_{i,pl,pr} - f(i)|$, subject to the following constraints: (1) $p_l$ (resp., pr) starts at $(l_{start}, 0)$ (resp., $(r_{start}, 0)$) and ends at $(l_{end}, H)$ (resp., $(r_{end}, H)$), (2) (the steepness constraint) both $p_l$ and $p_r$ are c-steep paths, and (3) (the closeness constraint) $|l_{i,pl,pr} - f(i)| \leq \Delta$ for all $i = 1, 2, \ldots, n$.

Figure 1B:
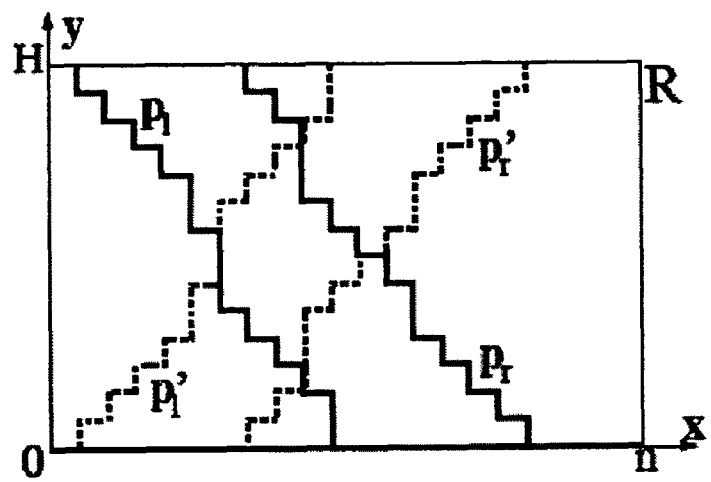
Figure 1C:
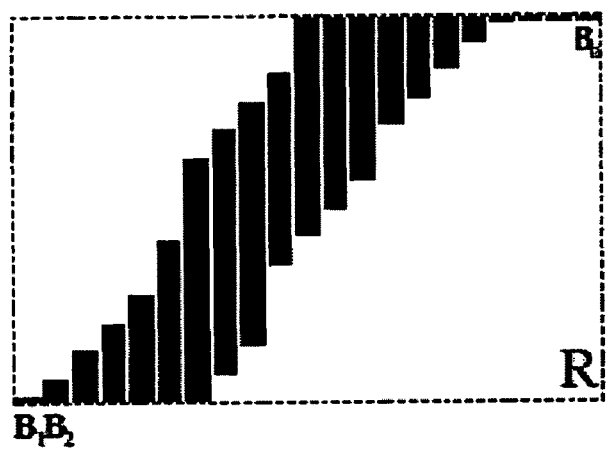

Without loss of generality, it is assumed that $l_{start} \leq l_{end}$ and $r_{start} \leq r_{end}$, so that the two sought paths $p_l$ and $p_r$ are both xy-monotone increasing paths. Otherwise, the CCPP problem can be transformed to a new CCPP problem that satisfies this condition. By flipping (FIGS. 1A-1B) one or both of the optimal paths for this new problem, two optimal paths are obtained for the original CCPP problem.

Algorithm for the Case where $l_{end} \geq r_{start}$

It is to be noted that the algorithm can be adapted easily to handle the other case in which $l_{end} < r_{start}$. The region $P(p_l, p_r)$ is a rectilinear xy-monotone polygon in $R_g$ and consists of a sequence of n vertical bars. Thus, the CCPP problem can be solved by transforming it to computing a shortest path in a directed acyclic graph, DAG G'. The DAG G' (FIG. 2A-2D) also contains a source s, a sink t, and n layers of vertices, $L'_1$, $L'_2 \ldots, L'_n$, which are defined as follows to satisfy the additional geometric constraints of the CCPP problem:

$$L'_i \begin{cases} \{[\alpha, \beta]^{(i)} \mid \alpha = \beta = 0 \text{ and } |\beta - \alpha - f(i)| < \Delta\} & \text{if } 1 \leq i \leq l_{start} \\ \{[\alpha, \beta]^{(i)} \mid 0 = \alpha < \beta \leq H - c \text{ and } |\beta - \alpha - f(i)| < \Delta\} & \text{if } l_{start} < i \leq r_{start} \\ \{[\alpha, \beta]^{(i)} \mid c \leq \alpha \leq \beta \leq H - c \text{ and } |\beta - \alpha - f(i)| < \Delta\} & \text{if } r_{start} < i \leq l_{endt} \\ \{[\alpha, \beta]^{(i)} \mid c \leq \alpha < \beta = H \text{ and } |\beta - \alpha - f(i)| < \Delta\} & \text{if } l_{end} < i \leq r_{end} \\ \{[\alpha, \beta]^{(i)} \mid \alpha = \beta = H \text{ and } |\beta - \alpha - f(i)| < \Delta\} & \text{if } r_{end} < i \leq n \end{cases} \quad \text{Eq. (1)}$$

Figure 3A:
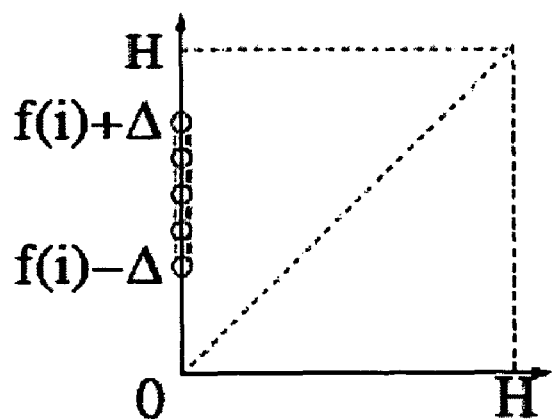
FIGS. 3A-3C illustrate the geometry of the vertex layer $L'_i$ of the DAG G' for $l_{start} \leq i \leq r_{start}$, $r_{start} \leq i \leq l_{end}$, and $l_{end} < i \leq r_{end}$. In each figure, all vertices in the vertex layer $L_i$ (or $L'_i$) are mapped to circled points on the 2-D plane; these points form all the lattice points in a convex polygon (possibly degenerated to a line segment) marked by the shaded area.
Figure 3B:
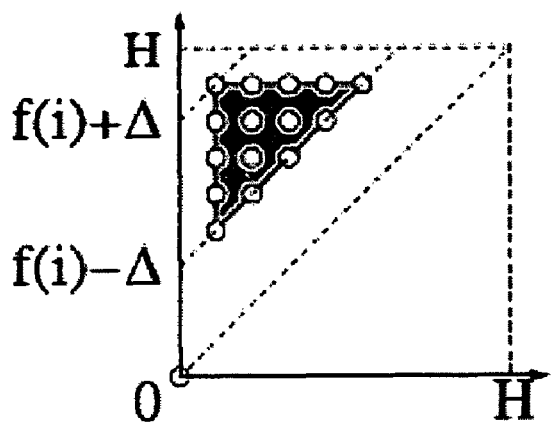
Figure 3C:
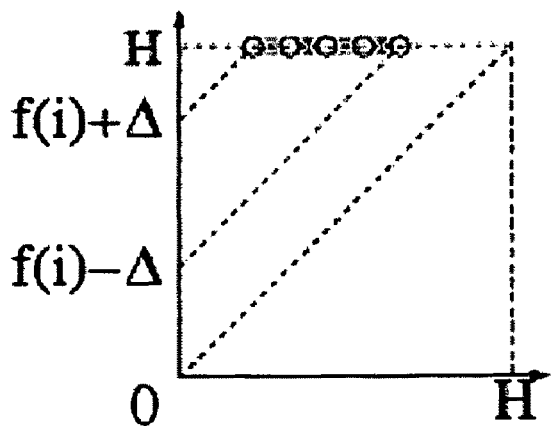

The weight of a $[\alpha, \beta]^{(i)}$ is defined as $\omega'([\alpha, \beta]^{(i)}) = \beta - \alpha - f(i)$ and the edges of G' are defined based on the same domination relation $D(\bullet, \bullet)$. A shortest s-to-t path in G corresponds to an optimal solution for the CCPP problem and, further, the vertices and edges of G0 have geometric properties similar to those of dominated sets (FIGS. 3A-3C). Such similar dominated sets may be $D(H,H)$, $D(\alpha,H)$ ($0 < \alpha < H$), $D(0,H)$, $D(\alpha,\beta)$ ($0 < \alpha \leq \beta < H$) $D(0,\beta)$ ($0 < \beta < H$), and $D(0, 0)$. Thus the shortest path computation can be sped up and the CCPP algorithm takes $O(nH\Delta)$ time.

EXAMPLE 2

Computing the Complete Set of all CCPP Problem Instances
Overview of the Algorithm Given f, n, H, $\Delta$, and c, CCPP problem instances are solved on f, n, H, $\Delta$, c, $l_{start}$, $r_{start}$, $l_{end}$, and $r_{end}$ for all possible combinations of $l_{start}$, $r_{start}$, $l_{end}$, and $r_{end}$. Without loss of generality, only those combinations which satisfy $l_{start} \leq l_{end}$ and $r_{start} \leq r_{end}$ are considered. All problem instances are classified into two subsets $S_1$ and $S_2$, with $S_1$ (resp., $S_2$) containing those with $l_{end} \geq r_{start}$ (resp., $l_{end} < r_{start}$).

Solving all CCPP Instances in $S_1$

It is to be noted that this approach can be adapted easily to solve all instances in $S_2$. Since $0 \leq l_{start} \leq r_{start} \leq l_{end} \leq r_{end} \leq n$, there are totally $N = \Theta(n^4)$ problem instances, denoted by $l_1$, $l_2, \ldots, l_N$. Let $1^{(k)}_{start}$, $r^{(k)}_{start}$, $1^{(k)}_{end}$, and $r^{(k)}_{end}$ be the corresponding specification for the problem instance lk. An instance $l_k$ ($1 \leq k \leq N$) corresponds to a shortest path problem on a vertex-weighted DAG, denoted by $G'_k$, of $O(nH\Delta)$ vertices and $O(nH^2\Delta^2)$ edges. The key observation is that $G'_k$ can be transformed into an edge-weighted DAG, denoted by $\hat{G}_k$, with only $O(\Delta)$ vertices and $O(\Delta^2)$ edges.

The algorithm consists of two main steps. First, prepare the weights of all edges in $\hat{G}_1, \hat{G}_2, \ldots,$ and $\hat{G}_N$ ($O(\Delta^2)$ edges for each $\hat{G}_k$). The weights of all the $O(n^4\Delta^2)$ edges are implicitly computed and stored in a batch fashion, in totally $O(n^2H^2)$ time, such that for any edge, its weight can be reported in $O(1)$ time. Second, a shortest path is computed in $\hat{G}_1, \hat{G}_2, \ldots,$ and $\hat{G}_N$, respectively. It is shown that each $\hat{G}_k$ ($1 \leq k \leq N$) is a DAG satisfying the Monge property (1-2,4). Since the weight of any edge can be obtained in $O(1)$ time, a shortest path in $\hat{G}_k$ takes only $O(\Delta)$ time to compute. The algorithm thus takes $O(n^2H\Delta^2 + n^4\Delta)$ time, improving the straightforward $O(n^5H\Delta)$ time algorithm, i.e., applying the CCPP algorithm $N = O(n^4)$ times) by a factor of $\min\{nH, n^3/\Delta\}$.

The Graph Transformation

For fixed $l_{start}$, $l_{end}$, $r_{start}$, and $r_{end}$ ($0 \leq l_{start} \leq r_{start}$ $l_{end} \leq r_{end} \leq n$), let 1 be the corresponding CCPP problem instance and $G' = (V(G'), E(G'))$ be the vertex-weighted DAG defined in Example 1 for solving l. For u is an element of $V(G)$, denote its weight by $\omega'(u)$. For a path p in G', the weight $\omega'(p)$ of p is defined as $\omega'(p) = \Sigma_{u \text{ is element of } p} \omega'(u)$. For u, v is an element of $V(G')$, denote by $\pi'(u, v)$ a shortest u-to-v path in G'.

Figure 2B:
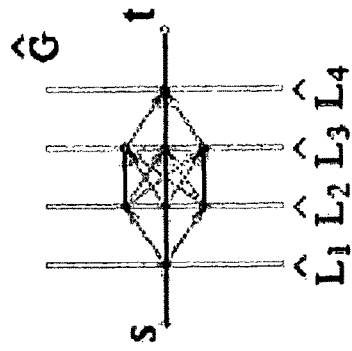
FIGS. 2A-2D illustrate the transformation of G' into ^G (FIGS. 2A-2B) and the layered DAGs $G_{i1,i1+1}$, $G_{i1,i1+2}$, and $G_{i1,n}$ (FIG. 2C) where each vertex layer is represented by a vertical line segment, and the set of edges from one vertex layer to the next layer is represented by an arrow and the DAG Gi1 after merging the DAGs $G_{i1,i1+1}$, $G_{i1,i1+2}$, and $G_{i1,n}$ (FIG. 2D).
Figure 2A:
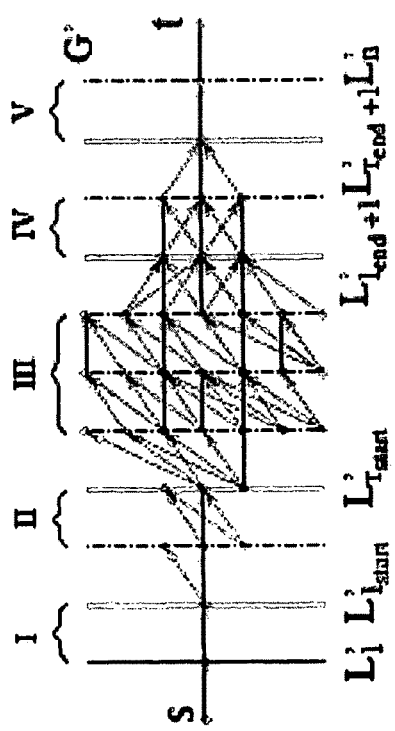
Figure 2D:
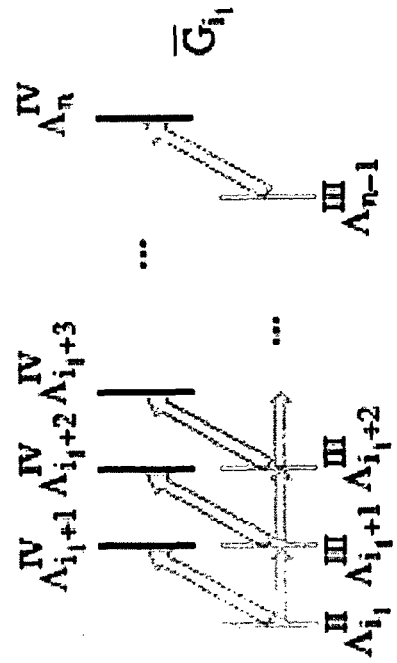
Figure 2C:
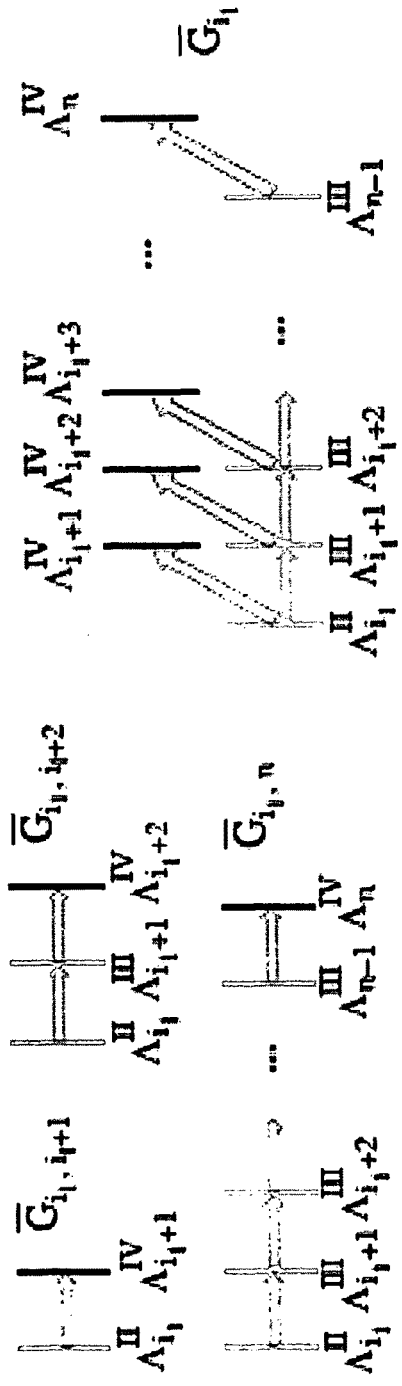

An edge-weighted directed graph $\hat{G} = (V(\hat{G}), E(\hat{G}))$ is constructed from G' as follows (FIGS. 2A-2B). The vertex set $V(\hat{G})$ is a subset of $V(\hat{G})$, and consists of two dummy vertices s and t and four vertex layers:

$$\hat{L}_1 \triangleq L'_{l_{start}}, \hat{L}_2 \triangleq L'_{r_{start}}, \hat{L}_3 \triangleq L'_{l_{end}+1}, \text{ and } \hat{L}_4 \triangleq L'_{r_{end}+1}.$$

The edge set $E(\hat{G})$ is simply $$\cup_{t-1}^3 (\hat{L}_t \times \hat{L}_{t+1}) \cup (\{s\} \times \hat{L}_1) \cup (\hat{L}_4 \times \{t\}).$$

Thus, the subgraph of $\hat{G}$ between any two consecutive vertex layers is a complete bipartite graph. For each edge (u, v) is an element of $E(\hat{G})$, a weight $\hat{\omega}(u, v) = \omega'(\pi'(u, v)) - \omega'(u)$ is assigned to it, i.e., the weight of a shortest u-to-v path in G' minus the vertex weight of u. For convenience, $\hat{\omega}(u, v) \triangleq +\infty$ if there is no path from u to v in G'.

$\hat{G}$ is an edge-weighted DAG and has $O(\Delta)$ vertices and $O(\Delta^2)$ edges (by the definition of $L'_i$ in Example 1). Define the weight $\hat{\omega}(p)$ of a path p in $\hat{G}$ as $\hat{\omega}(p) = \Sigma_{e \text{ is an element of } p} \hat{\omega}(e)$. A shortest s-to-t path in G' is closely related to a shortest s-to-t path in $\hat{G}$. In fact, it is not difficult to show that if $p' = s \to u_1 \to u_2 \to \ldots \to u_n \to t$ is a shortest s-to-t path in G', then $\hat{p} = s \to u_{lstart} \to u_{rstart} \to u_{lend+1} \to u_{rend+1} \to t$ is a shortest s-to-t path in $\hat{G}$, with $\hat{\omega}(\hat{p}) = w'(p'')$ This is due to the optimal-substructure property of shortest paths, i.e., any subpath of a shortest path is also a shortest path. Moreover, if $s \to v_2 \to v_3 \to v_4 \to t$ is a shortest s-to-t path in $\hat{G}$, then $$s \xrightarrow{\pi'(s,v_1)} v_1 \xrightarrow{\pi'(v_1,v_2)} v_2 \xrightarrow{\pi'(v_2,v_3)} v_3 \xrightarrow{\pi'(v_3,v_4)} v_4 \xrightarrow{\pi'(v_4,t)} t$$

is a shortest s-to-t path in G'.

Before explaining why the vertex layers $L'_{lstart}$, $L'_{rstart}$, $L'_{lend+1}$, and $L'_{rend+1}$, from G' for the construction of $\hat{G}$ were chosen, Equation (1) must be reviewed. Observe that if i is fixed and $l_{start}$, $r_{start}$, $_{lend}$, and $r_{end}$ are temporarily viewed as parameters, then Equation (1) implies that the i-th vertex layer in any G ($1 \leq k \leq N$) is in exactly one of five possible states, denoted by $\Lambda_i^{(I)}$, $\Lambda_i^{(II)}$, $\Lambda_i^{(III)}$, $\Lambda_i^{(IV)}$, and $\Lambda_i^{(V)}$, e.g., $\Lambda_i^{(I)}$ if $1 \leq i \leq l_{start}$). For a fixed k ($1 \leq k \leq N$), in the DAG $G'_k$, the i-th vertex layer L is of type I if $L=\Lambda_i^{(I)}$. The type II, III, IV, and V vertex layers are defined similarly.

Clearly, in the DAG G', all vertex layers between s and $L'_{lstart}$, $L''_{lstart}$ and $L_{rstart}$, $L''_{rstart}$ and $L'_{lend+1}$, $L'_{lend+1}$, and $L'_{rend+1}$, and $L'_{rend+1}$ and t are of type I, II, III, IV, and V, respectively (FIG. 2A). This implies an interesting property: For any edge (u, v) of $\hat{G}$, all vertex layers between u and v in G' are of the same type. As will be shown, this property plays a key role in speeding up the computation of the weights of all edges in the transformed DAGs $\hat{G}_1, \hat{G}_2, \ldots \hat{G}_N$. It should be pointed out that for one DAG G', although $\hat{G}$ is of a much smaller size than G', the weights of the edges of $\hat{G}$ are costly to compute. Thus transforming G' to $\hat{G}$ will not yield a faster algorithm for solving a single CCPP problem instance.

Computing the Edge Weights for all Transformed DAGs

It is demonstrated herein how to compute the weights of all edges in the transformed DAGs $\hat{G}_1, \hat{G}_2, \ldots, \hat{G}_N$. Recall that the weight of an edge in $\hat{G}_k$ corresponds to a one-pair shortest path problem instance on $G'_k$. Since every $\hat{G}_k$ has $O(\Delta^2)$ edges, there are in total $O(n^4\Delta^2)$ edges in $\hat{G}_1, \hat{G}_2, \ldots, \hat{G}_N$, corresponding to $O(n^4\Delta^2)$ one-pair shortest path problem instances.

It is stated that the $O(n^4\Delta^2)$ edges actually correspond to only $O(n^2\Delta^2)$ distinct one-pair shortest path problem instances. For any k that is an element of $\{1, 2, \ldots, N\}$ and for any edge (u, v) that is an element of $\hat{G}_k$, denote by SP(u, v, k) the corresponding one-pair shortest path instance, i.e., finding a shortest u-to-v path in $G'_k$. Considering the indices of the vertex layers in which u and v lie in $\hat{G}_k$ respectively, there are five cases. Only the most typical case, in which u (resp., v) lies in the 2nd (resp., 3rd) layer of $\hat{G}_k$ is discussed. For this case, let $i_1=r^{(k)}_{start}$ and $i_2=l^{(k)}_{end+1}$; then u is an element of $\Lambda^{II}_{i1} \subseteq V(G'_k)$, v is an element of $\Lambda^{IV}_{i2} \subseteq V(G'_k)$, and all vertex layers between u and v in $G'_k$ are of type III (FIG. 2A). Let $G_{i1,i2}$ be a layered DAG whose vertices consist of the vertex layers $\Lambda^{II}_{i1}, \Lambda^{III}_{i1+1}, \Lambda^{III}_{i1+2}, \ldots, \Lambda^{III}_{i2-1}$, and $\Lambda^{IV}_{i2}$, in this order, and whose edges are defined based on the same domination relation $D(\bullet, \bullet)$.

Clearly, SP(u, v, k) is equivalent to finding a shortest u-to-v path in $G_{i1,i2}$. Since $i_1$ (resp., i2) ranges from 1 to n, $G_{i1,i2}$ has $O(n^2)$ possible choices. Note that u (resp., v) belongs to the layer $\Lambda^{II}_{i1}$ (resp., $\Lambda^{IV}_{i2}$), which contains $O(\Delta)$ vertices for any $i_1$ (resp., $i_2$). It follows that SP(u, v, k) has $O(n^4\Delta^2)$ possible choices for the case where u (resp., v) lies in the 2nd (resp., 3rd) layer of $\hat{G}_k$. Other cases can be analyzed similarly. Since there are five cases, SP(u, v, k) has $O(n^2\Delta^2) \times O(1) = O(n^2\Delta^2)$ possible choices in total.

Since there are only $O(n^2\Delta^2)$ distinct one-pair shortest path problem instances, it is preferred to implicitly compute and store the weight of each edge of $\hat{G}_1, \hat{G}_2, \ldots, \hat{G}_N$. More specifically, distinct one-pair shortest path instances are solved and the corresponding shortest paths along with their lengths are stored, so that given an edge (u, v) of any $\hat{G}_k$, its weight can be reported in O(1) time.

It is demonstrated how to solve the $O(n^2\Delta^2)$ distinct one-pair shortest path problem instances in a batch fashion. First a set of one-pair shortest path instances are combined into one single-source shortest path problem instance. Second, a set of single-source shortest path instances are solved in one shot by "merging" the underlying DAGs into one DAG of a comparable size. This approach is illustrated by showing how to solve the one-pair shortest path instances in $G_{i1,i2}$ (as defined in the previous paragraph) for all $i_1$, $i_2$. Each instance is specified by a source vertex u is an element of $\Lambda^{II}_{i1}$ and a destination vertex v is an element of $\Lambda^{IV}_{i2}$. Recall that $G_{i1,i2}$ contains the vertex layers $\Lambda^{II}_{i1}, \Lambda^{III}_{i1+1}, \Lambda^{III}_{i1+}, \ldots, \Lambda^{III}_{i2-1}$, and $\Lambda^{IV}_{i2}$. For a fixed $i_1$, the layered DAGs $G_{i1,i2}$, for all $i_2=i_1+1, \ldots, n$, can be merged into one DAG, simply denoted by $G_{i1}$ (FIGS. 5C-5D). For any vertex u is an element of $\Lambda^{II}_{i1}$, its single-source shortest paths can be computed in $G_{i1}$, in $O(nH\Delta)$ time as in the CCPP algorithm. Since $|\Lambda^{II}_{i1}|=O(\Delta)$ and $i_1$ ranges from 1 to n, the one-pair shortest path instances in $G_{i1},i2$ can be solved for all $i_1$, $i_2$, in $O(nH\Delta) \times O(n) \times O(\Delta) = O(n^2\Delta^2)$ time.

Shortest Path Computation on the Transformed DAGs

The algorithm for computing a shortest path in the DAG $\hat{G}$ as defined as defined above is presented. The key idea is to show that $\hat{G}$ satisfies the Monge property [1, 2, 4], and thus a shortest path in $\hat{G}$ can be computed by examining only a small portion of its edges.

Consider the vertex layers $\hat{L}_2$ and $\hat{L}_3$ of $\hat{G}$. Clearly, $\hat{L}_2=L'_{rstart}=\{[\alpha, \beta]^{(rstart)} 0 \leq \alpha \leq \beta <= H-c$ and $|\beta-\alpha-f(rstart)| \leq \Delta\}=\{[0, \beta]^{(rstart)} | 0 \leq \beta <= H-c$ and $|\beta-f(rstart)| \leq \Delta\}$). Thus $\hat{L}_2$ can be written as $\hat{L}_2=\{u_1, u_2, \ldots, u_{|\hat{L}2|}\}$, where $u_k=[0, \beta_k]^{(rstart)} (1 \leq k \leq |\hat{L}_2|)$ and $0 < \beta_1 < \beta_2 < \ldots < \beta_{|\hat{L}2|} \leq H-c$. Similarly, write $\hat{L}_3$ as $\hat{L}_3=\{v_1, v_2, \ldots, v_{|\hat{L}3|}\}$, where $v_k=[_k, H]^{(lend+1)} (1 \leq k \leq |\hat{L}_3|)$ and $c \leq \alpha_1 < \alpha_2 < \ldots < \alpha_{|\hat{L}3|} < H$. The following lemma shows the properties of the edges from the vertices on $\hat{L}_2$ to $\hat{L}_3$ in $\hat{G}$.

Lemma: (A) Let $u_i$ (resp., $v_j$) be a vertex on $\hat{L}_2$ (resp., $\hat{L}_3$) of $\hat{G}$, with $1 \leq i \leq |\hat{L}_2|$ (resp., $1 \leq j \leq |\hat{L}_3|$). If $\hat{\omega}(u_i, v_j)=1$, then for any j'<j (resp., i'>i), $\hat{\omega}(u_i, v_{j'})=\infty$ (resp., $\hat{\omega}(u_{i'}, v_j)=\infty$). (B) Let $u_i$, $u_{i'}$ (resp., $v_j$, $v_{j'}$) be two vertices on $\hat{L}_2$ (resp., $\hat{L}_3$) of $\hat{G}$, with $1 \leq i<i' \leq |\hat{L}_2|$ (resp., $1 \leq j<j' \leq |\hat{L}_3|$). If both edges $e_1=(u_i, v_{j'})$ and $e_2=(u_{i'}, v_j)$ have finite weights, then edges $e_3=(u_i, v_j)$ and $e_4=(u_{i'}, v_{j'})$ also both have finite weights. Moreover, $\hat{\omega}(e_3)+\hat{\omega}(e_4) \hat{\omega}(e_1)+\hat{\omega}(e_2)$.

The lemma implies that the matrix A of size $|\hat{L}_2| \times |\hat{L}_3|$, with $=\hat{\omega}(u_i, v_j)$, is a Monge matrix. Note that for any i and j, $\hat{\omega}(u_i, v_j)$ can be reported in O(1) time as described above. Thus in $\hat{G}$, once the shortest paths from s to all vertices in $\hat{L}_2$ are computed, using the Monge matrix multiplication algorithms [1, 2, 4], the shortest paths from s to all vertices in $\hat{L}_3$ can be computed in $O(\Delta)$ time. Observe that outside the subgraph of $\hat{G}$ between the vertex layers $\hat{L}_2$ and $\hat{L}_3$ (FIG. 2B), there are only $O(\Delta)$ edges of $\hat{G}$. Hence a shortest s-to-t path in $\hat{G}$ can be computed in $O(\Delta)$ time. Thus, the following theorem is:

Given a non-negative function $f$ defined on $\{1, 2, \ldots, n\}$ and positive integers c, H, and $\Delta (\Delta \leq H)$, the complete set of the CCPP problem instances is computable in $O(n^2H^2+n4)$ time.

EXAMPLE 3

Unconstrained Intensity Optimization in Single-arc Dose Painting

The first planning step for single arc dose painting is unconstrained intensity optimization. Different algorithms can be used for achieving this step (11-13). Suitable algorithms are available in the relevant literature (8,10). As with IMAT, an arc is approximated with multiple fixed radiation beams evenly spaced every 5-10 degrees (5).

EXAMPLE 4

Leaf-sequencing in Single-arc Dose Painting

Step two in single-arc dose painting is the conversion of the optimized beam intensities into connected field apertures. The goal is to find a set of connected field shapes that when delivered dynamically based on linear interpolation between the apertures, will result in minimum discrepancy to the optimized intensity profile. For leaf sequencing, a hybrid approach has been developed. For simple cases the method called line segment approximation on component intensity profiles is appropriate. For more complicated cases, leaf position and aperture weight optimization and leaf position and aperture weight optimization may be used.

Line Segment Approximation to Component Intensity Profiles

This method is based on a "sliding window" technique. Recognizing that any intensity pattern can be delivered by sliding a varying aperture in either direction, each of the intensity patterns can be converted into "sliding window" dynamic control points. The only constraint to ensure the interconnectedness of the intensity patterns is that in the next interval, the direction of the "sliding window" has to be in the opposite direction. Accordingly, the apertures defined by the multi-leaf collimator (MLC) sweep back and forth, completing one cycle in every two intervals.

The conversion from fluence distributions to MLC "sliding window" delivery is illustrated by FIGS. 4A-4B. For a given arbitrary intensity distribution aligned with a pair of opposing leaves, such as that shown in FIG. 4A, initially, a separation is made between the portion to be delivered by the leading leaf (right leaf) and that to be delivered by the trailing leaf (left leaf). With the radiation source turned on, for a fixed left leaf position, moving the right leaf towards the right will create a negative gradient. Likewise, for a fixed right leaf position, moving the left leaf towards the right will create a positive intensity gradient. Therefore, the method first finds the points that separate the positive and negative gradients, as illustrated by the vertical lines. Then positive gradient portions are to the trailing profile and inverted negative gradient portions to the leading profile as shown on FIG. 4B. The vertical axis represents beam intensity in radiation monitor units (MUs), which is also time for a given machine dose rate. With this separation, the profile may be defined as follows:

Original profile=Trailing Profile−Leading profile.

The separated profiles become the leading and trailing leaf positions as functions of time. If both leaves are moved according to FIG. 1B, the desired intensity profile will be created.

Inspection of FIG. 4B, reveals that for both leaves, there will be sections where the leaves are required to change positions with no elapsed time (the flat portions of the profiles). Accordingly, in order to make the dose delivery physically achievable, the minimum gradient required for leaf travel (governed by the maximum leaf traveling speed) is added to the flat portions, while the same amount is added to the other profile so that the difference between the two profiles is kept substantially constant (FIG. 4C). When this intensity profile is delivered, the apertures of varying width formed by both leaves will move smoothly from the left to the right. Such smooth motion is the origin of the term "sliding window technique". The left leaf can alternatively be considered to be the leading leaf and the right leaf to be the trailing leaf, thereby delivering the same intensity distribution by sliding the "window" from the right to the left.

With the current art of dynamic MLC leaf sequencing, the control-points are generated by evenly dividing the total monitor units (MUs) required by the number of segments, which is normally relatively large (~50). Rather than a pure "sliding window" leaf-sequencing as described in FIGS. 4A-4B, it is also possible to sequence the optimized intensity maps in a "sliding window" fashion using a graph algorithm known and standard in the art. Because the treatment apparatus, linac and MLC, performs the linear interpolation automatically, accurate delivery is ensured if the vertices that join two lines of different slopes are used as control points. Therefore, the gradient turning positions of the original intensity profile (the intercepts of the vertical lines with the profiles) are used as the initial estimations of the control points. In essence, the original component intensity profiles are approximated with connected line segments. These initial control points are used as the input to the next step of the leaf sequencing process.

As indicated in FIGS. 4A-4B, the apertures selected from the sliding window leaf sequence are naturally interconnected within each planning interval. The apertures within each interval will move either left to right or right to left. To make it easier to connect all intervals into one arc, the apertures are sequenced in such a way that: 1) the MLC leaves move in opposite directions in any two neighboring angular intervals; and 2) the two aperture shapes connecting any two angular intervals do not violate the physical constraints of the MLC (i.e., the shapes are not so drastically different as to require large MLC movements). Because any intensity map can be delivered dynamically in either left-to-right or right-to-left leaf motion, the direction of MLC motion alternates between neighboring beams and the aperture shape connectivity is considered throughout the arc. As a result, the shape-varying beam aperture (or "dynamic window") slides back and forth while the gantry rotates around the patient.

Leaf Position and Aperture Weight Optimization

One of the concerns presented by method using line segment approximation to component intensity profiles is that for complex intensity distributions, using this method alone may result in a plan with very high machine beam-on times and may requires too many control points to maintain a very close dose conformity. Thus for more complicated cases, two alternative, and somewhat more complex, methods can be used, as described below.

Observe that during the delivery of a set of densely-spaced intensity patterns, each pair of MLC leaves will deliver a set of densely-spaced intensity profiles that are aligned with this leaf pair. The method comprises the following key steps:

First, for every pair of MLC leaves, each of its aligned intensity profiles is converted into a set of k leaf openings using a geometric k-link shortest path algorithm with equal beam-on times that incurs the minimum error. Second, the leaf openings for the same pair of MLC leaves are connected together to form a single-arc of leaf openings using a geometric shortest path algorithm that ensures a smooth transition between adjacent leaf openings while minimizing the error incurred. Third, the single-arcs for each pair of MLC leaves are then combined to form the final single-arc treatment plan.

Figure 5A:
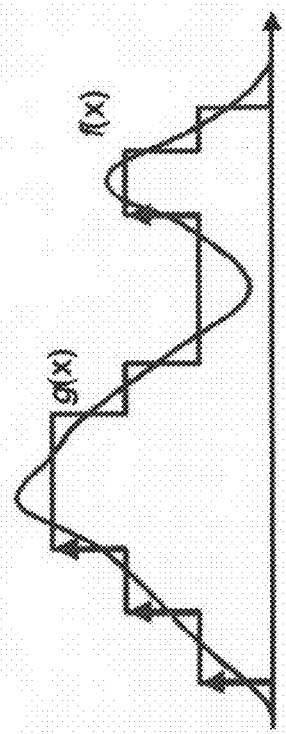
FIGS. 5A-5D illustrate steps of the shortest path graph algorithm for converting an intensity profile into k MLC leaf openings with the minimum error.
Figure 5B:
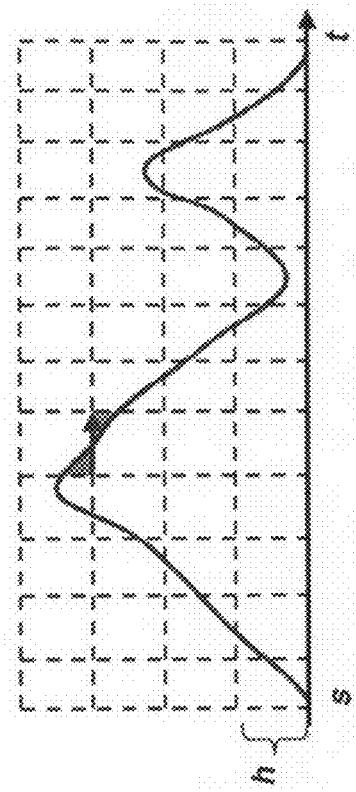
Figure 5C:
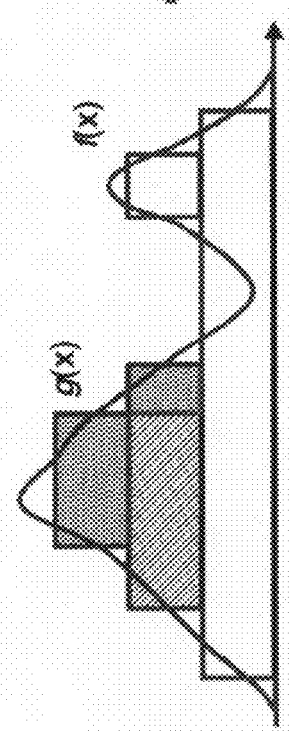
Figure 5D:
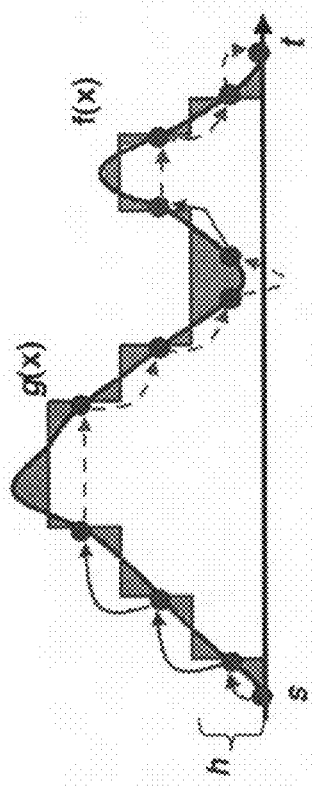

FIGS. 5A-5D illustrate the key idea of this step. In FIG. 5A, the optimized fluence profile is represented by the functional curve $f(x)$ and the resulting simplified profile is the rectilinear functional curve $g(x)$ that is deliverable by k=4 leaf openings with equal beam-on. The error here is the integral of the absolute difference between the two functions, $\int |f(x)-g(x)| dx$ (the shaded area in FIG. 5C). In FIG. 5A, each leaf opening is represented by a rectangle whose left and right ends are the positions of the MLC leaf pair and whose height is its beam-on time. The simplified intensity profile is created by "stacking up" these rectangles. Since all the leaf openings have the same beam-on time, i.e., the rectangles representing the leaf openings all have the same height, the resulting profile g(x) can have up to k upward edges and k downward edges, if we traverse the profile curve from left to right (FIG. 5B). This problem can be solved by searching for an optimal k-weight path in a graph capturing the geometry of the problem; the total cost of the path represents the error between the simplified profile and the input profile, and its weight indicates how many leaf openings are needed to create the simplified profile. FIG. 5C illustrates such a k-weight path, where the k upward edges are highlighted in red (solid if black and white) and the error is the area sum of the shaded regions.

To find such a k-weight path, a directed graph G is constructed as in FIG. 5D. Specifically, for each possible height h of the rectangles, a grid structure is imposed, whose vertical edge lengths are h and horizontal edge lengths are of the resolution size of the given intensity patterns. Each grid node is a vertex of the graph G. The lower leftmost grid node is the source vertex s of G, and the lower rightmost node is the sink vertex t. For any horizontal grid edge, we put an edge in G from left to right with a zero weight and a cost that is the error incurred when this edge is used by the resulting profile (FIG. 5D) for a horizontal edge and its cost, i.e., the shaded area). For each vertical grid edge, we put in G an upward edge with a unit weight and a downward edge with a zero weight. Observe that a k-weight optimal s-to-t path in G thus constructed yields a desired simplified profile. This optimal path problem can be solved by the constrained shortest path algorithm.

The k-link path algorithm above will convert each intensity profile into a simplified profile that can be deliverable by k leaf openings. For each simplified profile, there are potentially k! ways to break it up into leaf openings. In this algorithm, break each simplified intensity profile is broken into a set of canonical leaf openings. Specifically, a set of leaf openings is called canonical if only if for any two leaf openings [$l_i$, $r_i$] and [$l_j$, $r_j$] (where and $l_i$ and $l_j$ denote the left leaf positions, and $r_i$ and $r_j$ denote the right leaf positions), either $l_i \leq l_j$, $r_j \leq r_j$, or $l_i \geq l_j$, $r_j \geq r_j$. Intuitively, a set of canonical leaf openings can be sorted from left to right.

Figure 6A:
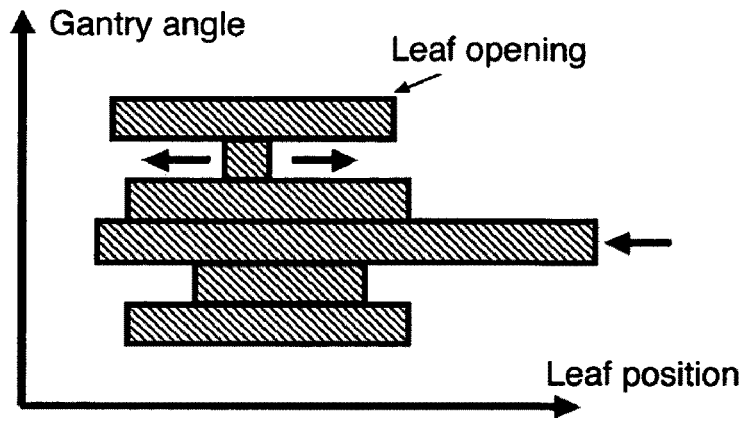
FIGS. 6A-6C illustrate a step of the shortest path graph algorithm for adjusting a one-dimensional IMAT arc.
Figure 6B:
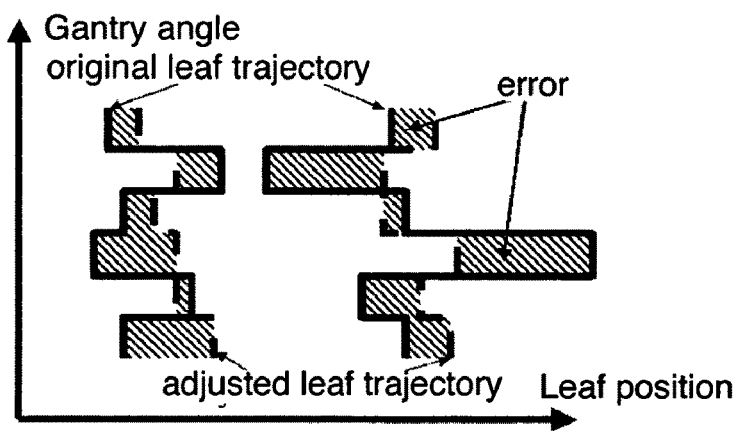
Figure 6C:
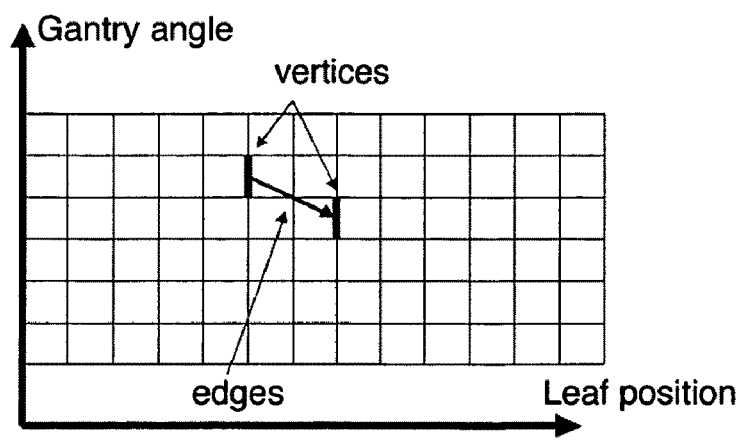

FIGS. 6A-6C illustrate the key concept for the second step, i.e., for combining the canonical leaf openings into arcs. When combining the leaf openings to form a single-arc, for each pair of leaves, its single-arc can be viewed as two curves, each representing the leaf trajectory as a function of the leaf position with respect to the gantry angles. The solid curves in FIG. 6B show the corresponding leaf trajectories of the single-arc illustrated in FIG. 6A. If this single-arc is not deliverable under the maximum leaf speed constraint, the arc has to be adjusted to make it deliverable while minimizing the error incurred by the adjustment.

Geometrically, the effect of the adjustment is to deform the original leaf trajectories into two new leaf trajectories. FIG. 6B gives such an adjustment where the original solid curves are changed to the dashed ones. The error is the area sum of the shaded regions. Since each leaf trajectory is a function of the leaf position with respect to the gantry angles, it can be viewed as a path of leaf positions along the gantry angle direction. This implies that the above adjustment problem can be solved by modeling it as a shortest path problem, in which the cost of a path is the error of the adjustment. FIG. 6C shows the graph construction. Each possible leaf position is a vertex, and two vertices for adjacent gantry angles are connected by an edge if they satisfy the maximum leaf speed constraint. Each vertex has a cost for the error incurred when adjusting the corresponding original leaf position for its gantry angle using that vertex. Geometrically, this error corresponds to a shaded region in FIG. 6B. Hence, the problem of adjusting a single arc as originally planned into a deliverable arc becomes a shortest path problem.

The spacing of the apertures within each interval is also straightforward. This is because the apertures obtained for each angular interval can sorted from left to right. The angular interval can be evenly divided the by the number of apertures used to reproduce the intensity distribution. The apertures can be sequenced in such a way that: 1) the MLC leaves move in opposite directions in any two neighboring angular intervals; and 2) the two aperture shapes connecting any two angular intervals do not violate the physical constraints of the MLC, i.e., they are not so drastically different as to require large MLC movements. As the result, the shape-varying beam aperture slides back and forth while the gantry rotates around the patient. Since the apertures for different angular intervals are obtained with different dose rates, this single arc plan may require dose rate changes during the delivery.

Leaf Position and Aperture Weight Optimization

In some clinical cases, it may be desirable to construct a series of single-arc plans that represent a tradeoff between machine beam-on times and error between the delivered fluence and prescribed ideal fluences. In such a case, in the event that each of the previously described two methods fails to give a high quality plan, the following method described in this section may be used.

Consider FIGS. 7A-7B, and, for simplicity, assume that the MLC consists of only one pair of leaves. FIG. 7A shows a sample single-arc plan, where the red curve represents the left leaf trajectory and the blue curve represents the right leaf trajectory. Note that, since, in a single-arc plan, the MLC keeps moving as the gantry rotates 360° around the patient at constant speed, the leaf trajectory is actually a functional curve between gantry angle and MLC leaf positions. For each small angular interval $\Delta\theta$ (typically)5°-10°, the portions of the leaf trajectories deliver a fluence profile (FIG. 7B).

Figure 8A:
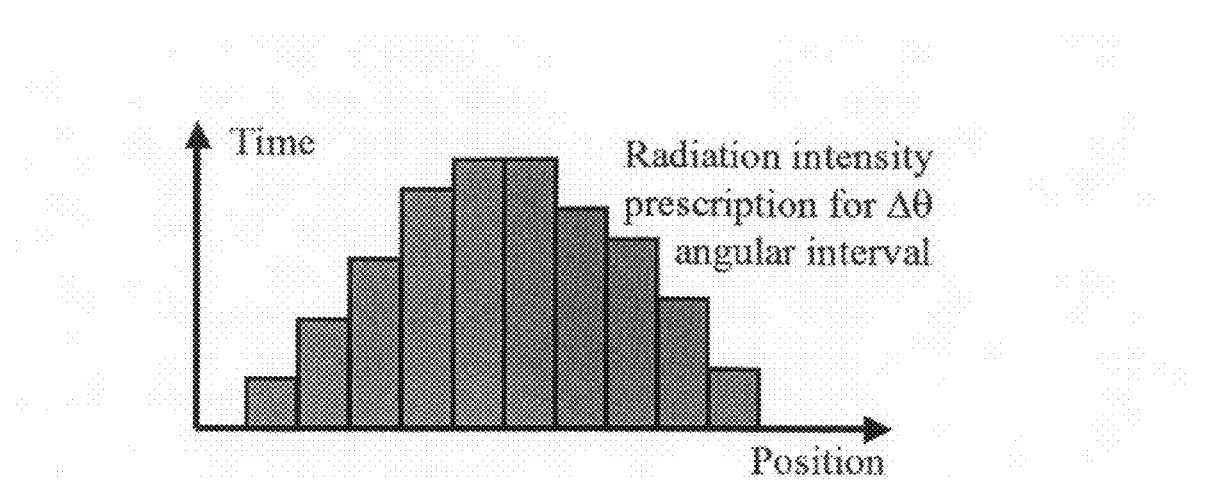
FIGS. 8A-8B illustrate leaf position and aperture weight optimization using the shortest path graph algorithm.
Figure 8B:
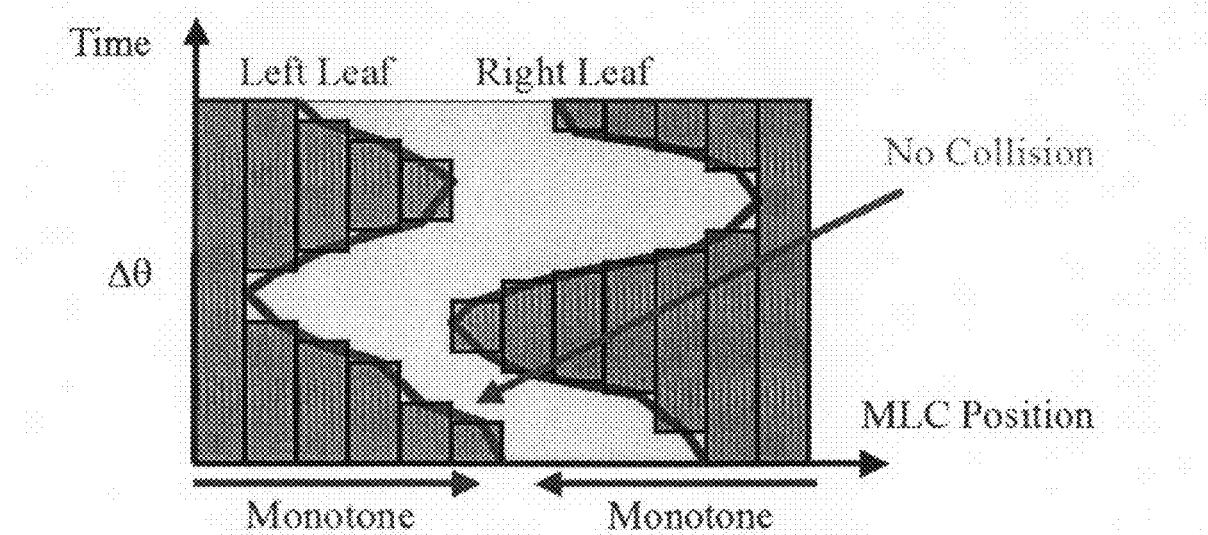

The above observation forms the basis for the following method:

First, for each given error bound, the intensity profile in every planning beam interval for each pair of MLC leaves is converted to a set of candidate sequences of leaf openings using a shortest path algorithm with minimized error subject to the error bound. These candidate sequences may differ from each other in the starting and/or ending leaf openings. FIG. 8B shows a candidate sequence for the intensity profile as shown in FIG. 8A with certain starting and ending leaf trajectory positions. The goal here is to construct a graph whose nodes are the candidate leaf trajectories. Each node will have a cost associated with it, which is the error of the trajectory when delivering its own profile. Two nodes from adjacent angular intervals are connected together if their transitions are smooth. A shortest path here yields an optimal single-arc plan. To improve the running time, one limits the number of candidate trajectories. e.g., by restricting the trajectories to be monotonic.

Second the sequences computed in the first step are connected together to form a single arc of leaf openings using a shortest path to ensure a smooth transition of the leaf positions between adjacent planning beam intervals while minimizing the total error incurred. Third, the single arcs for each pair of MLC leaves are then combined to form the final single-arc treatment plan.

Since the above method can compute a single-arc plan subject to an error bound, the method can compute a tradeoff between error and number of control points, or error and machine beam-on times.

Example 4

Single Arc Sequencing

Figures 9A, 9B:
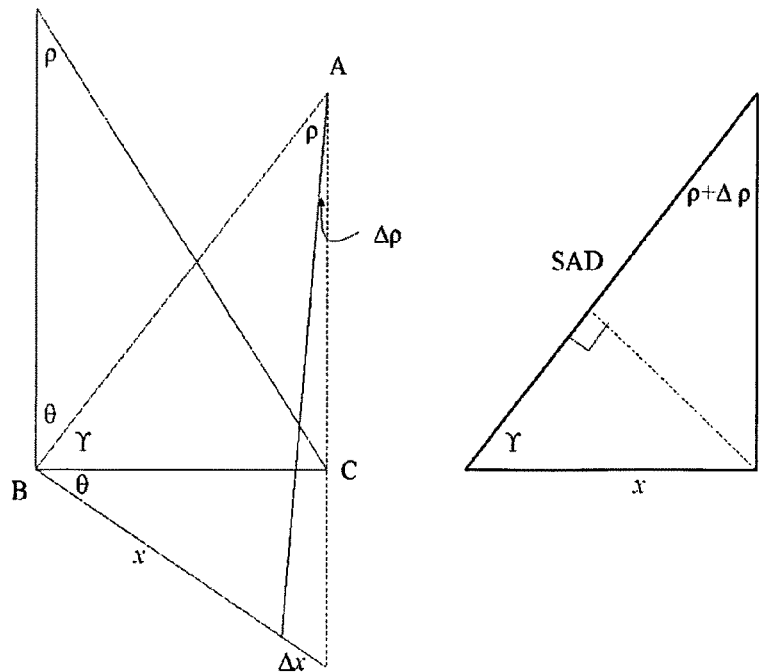
FIGS. 9A-9D illustrate field width adjustment on the right side (FIGS. 9A-9B) and on the left side (FIGS. 9C-9D).

Note that up to this point, the apertures are all at the designated planning angle at the center of the planning interval. When we move the aperture to another angle a few degrees away, the dose will change slightly. To maintain the dose delivered to the target, the apertures are adjusted as follows:

In FIG. 9A, AB is the radiation source to rotational center i.e. isocenter, distance, and BC=x is the x coordinate of the right leaf. If the same opening is delivered at angle r away, the same opening will not be able to cover the same width of target as originally intended. To cover the same target width, the aperture needs to be enlarged by Dx. FIG. 9B omits DABC for clarity. From FIGS. 9A-9B, the following equation may be written:

$$\tan(\rho + \Delta \rho) = \frac{x \cdot \sin \gamma}{SAD - x \cdot \cos \gamma}.$$

This yields:

$$x + \Delta x = SAD \cdot \tan(\rho + \Delta \rho) = SAD \cdot \frac{x \cdot \sin \gamma}{SAD - x \cdot \cos \gamma}.$$

Substituting $$\gamma = \frac{\pi}{2} - \theta,$$

the following is obtained:

$$x + \Delta x = SAD \cdot \frac{x \cdot \sin\left(\frac{\pi}{2} - \theta\right)}{SAD - x \cdot \cos\left(\frac{\pi}{2} - \theta\right)} = SAD \cdot \frac{x \cdot \cos \theta}{SAD - x \cdot \sin \theta}.$$

Figures 9C, 9D:
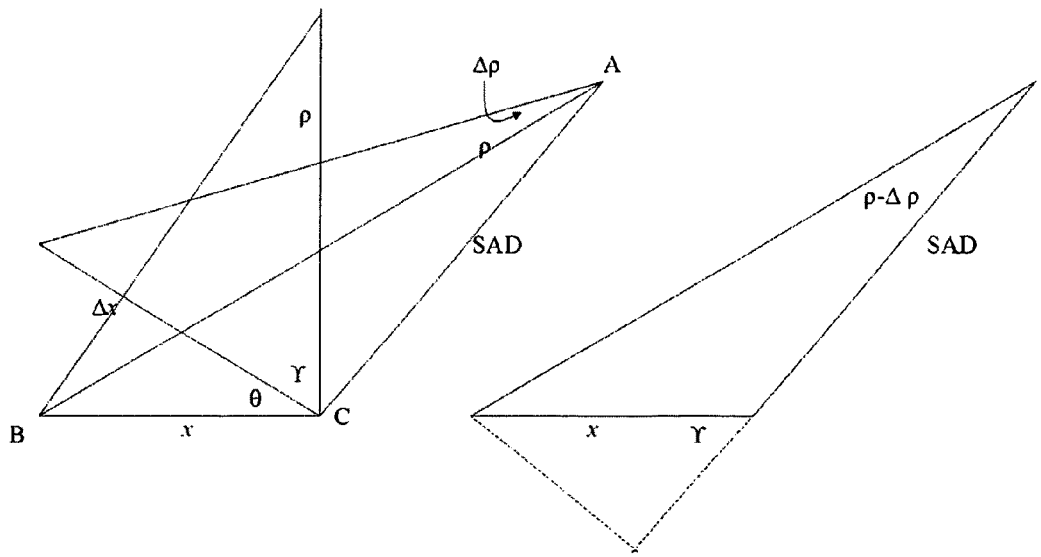

Similarly, the adjustment on the other side can be deduced. From FIGS. 9C-9D:

$$\tan(\rho - \Delta \rho) = \frac{x \cdot \sin \gamma}{SAD + x \cdot \cos \gamma}.$$

This gives:

$$x - \Delta x = SAD \cdot \tan(\rho - \Delta \rho) = SAD \cdot \frac{x \cdot \sin \gamma}{SAD + x \cdot \cos \gamma}.$$

Substituting $$\gamma = \frac{\pi}{2} - \theta,$$

the following is obtained:

$$x - \Delta x = SAD \cdot \frac{x \cdot \sin\left(\frac{\pi}{2} - \theta\right)}{SAD + x \cdot \cos\left(\frac{\pi}{2} - \theta\right)} = SAD \cdot \frac{x \cdot \cos \theta}{SAD + x \cdot \sin \theta}.$$

When the aperture is moved counterclockwise from the planned angle, r will be negative. Given these simple relationships, the new aperture widths can be set to provide the same coverage at the new angle as the original aperture provided at the planned angle. Alternatively or in addition to the above mentioned aperture shape adjustment for the apertures moved away from the planning angle, a simple aperture weight and shape optimization can be performed to further refine the single arc to deplete any potential rooms of improvement of the treatment plan quality.

EXAMPLE 5

Single Arc Painting for Cancer of Larynx

Figure 10A:
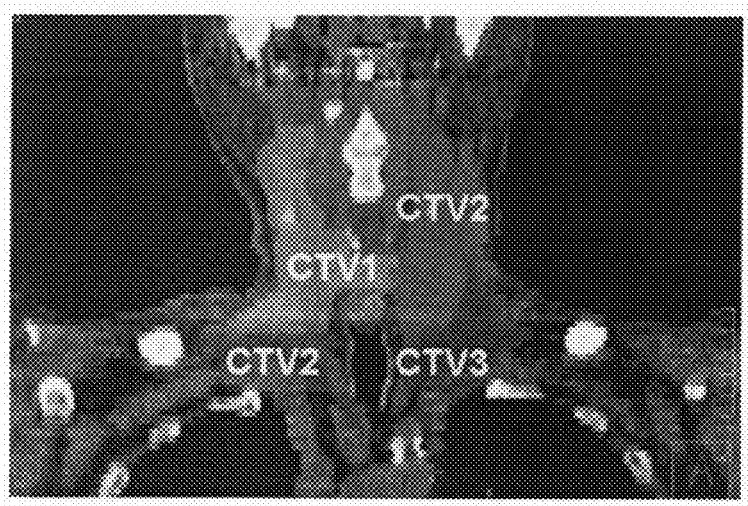
FIGS. 10A-10C illustrate a planned (FIGS. 10A-10B) and delivered (FIG. 10C) dose distribution for a complicated head and neck case with single arc dose painting.
Figure 10B:
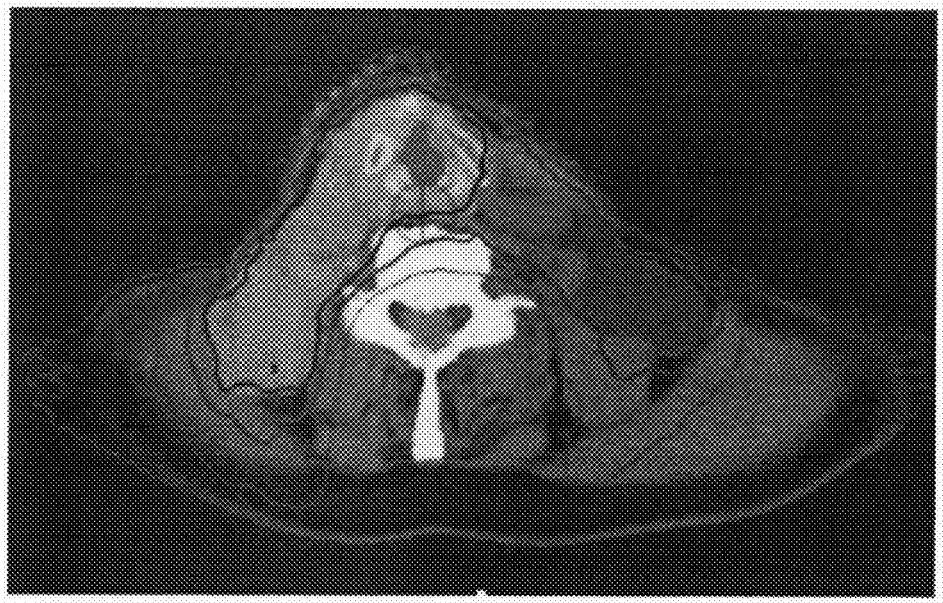
Figure 10C:
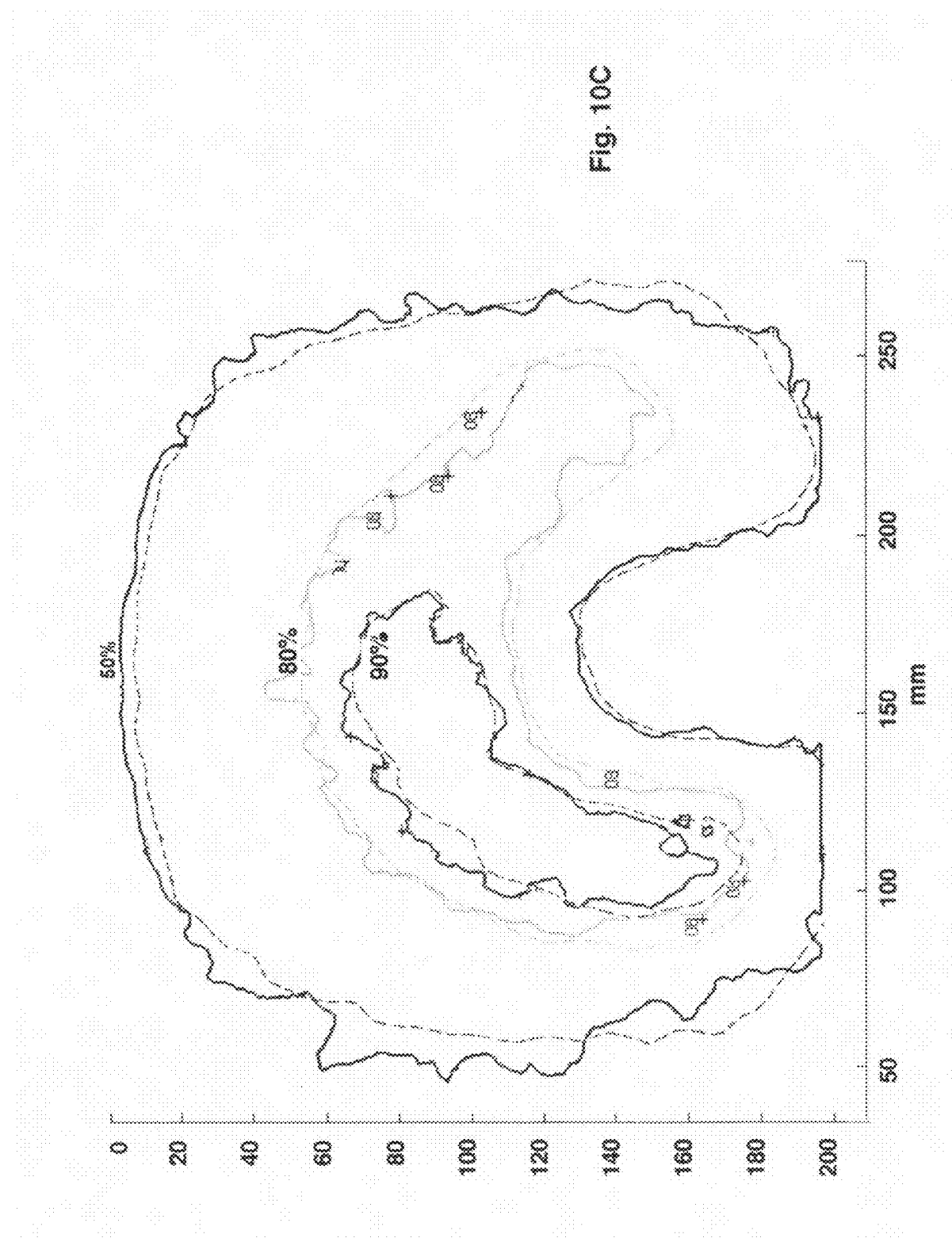

Sample plans were developed for several clinical cases. The plans were transferred to a Varian linear accelerator and delivered to a phantom. Comparison of the delivered and measured doses showed good agreement. One plan is for a larynx case with 3 targets, each with different dose specifications (FIG. 10A). FIG. 10B shows the dose distribution on a transverse slice at neck level resulting from the single-arc plan and FIG. 10C is the result of dose verification by delivering the single-arc plan to a phantom. Note that the phantom is different in size and shape from the patient and the calculated dose from the same plan is therefore also different.

THE FOLLOWING REFERENCES ARE CITED HEREIN

1. Bortfeld et al., Int J Rad Oncol Biol Phys, 28(3):723-730 (1994).
2. Boyer, A. & Yu, C., Seminars in Radiation Oncol 9(1):48-59 (1999).
3. Mackie et al., Med Phys, 20(6):1709-19 (1993).
4. Yu et al., Phys. Med. Biol., 40:769-787 (1995).
5. Yu, C. X., Phys. Med. Biol., 40:1435-49, (1995).
6. Yu et al., Int J Radiat Oncol Biol Phys 53(2):453-63 (2002).
7. Cho, P. S. & Marks, R. J. II, Phys. Med. Biol, 45(2):429-440 (2000).
8. Earl et al., Phys. Med. Biol. 48(8):075-89 (2003).
9. Cameron, C., Phys Med. 50(18):4317-36 (2005).
10. Shepard et al., Med. Phys. 34(2):464-470 (February 2007).
11. Brahme, A., Int J Radiat Oncol Biol Phys. 49(2):327-37 (2001).
12. Shepard et al., Physics in Medicine and Biology, 45(1):69-90 (1999).
13. Webb, S., Phys. Med. Biol. 39(12):2229-2246 (1994).

Any patents or publications mentioned in this specification are indicative of the level of those skilled in the art to which the invention pertains. Further, these patents and publications are incorporated by reference herein to the same extent as if each individual publication was specifically and individually incorporated by reference.

One skilled in the art would appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for designing a radiation treatment for a subject using single arc dose painting, comprising:
    providing an unconstrained optimization map which supplies intensity profiles of densely-spaced radiation beams;
    aligning each intensity profile to a pair of multiple leaf collimation (MLC) leaves;
    applying a shortest path algorithm to convert each pair of MLC leaves to a set of leaf aperture sequences, said set of leaf aperture sequences forming a shortest path single arc thereof; and
    connecting each single arc of leaf apertures to form a final treatment single arc path, thereby designing the single arc dose painting radiation treatment.

2. The method of claim 1, further comprising:
    delivering a continuous dose of radiation to the subject through each aperture during a single rotation along one or more final treatment single arc paths.

3. The method of claim 1, further comprising:
    adjusting a shape of the aperture as a radiation dose delivery angle changes along the final treatment arc.

4. The method of claim 1, wherein the paths of more than one single arc are non-coplanar.

5. The method of claim 1, wherein the apertures sweep back and forth along the single arc path during delivery of the radiation dose.

6. The method of claim 1, wherein sequencing leaf apertures comprises one or more of a line segment approximation on component intensity profiles leaf position, weight optimization of apertures and optimization of leaf position and aperture weight.

7. The method of claim 1, wherein the leaf aperture sequences in each set have one or both of a different starting or ending leaf aperture.

8. The method of claim 7, wherein a starting and ending position of a leaf aperture trajectory are fixed.

9. The method of claim 1, wherein multiple leaf collimation is dynamic.

10. The method of claim 1, further comprising
    irradiating a tumor in a subject with the continuous dose of radiation through sets of multiple leaf collimation (MLC) aperture sequences during a single rotation along one or more of the treatment single arc paths.

11. The method of claim 10, further comprising:
    adjusting a shape of the aperture as a radiation dose delivery angle changes along the treatment single arc path.

12. The method of claim 10, further comprising:
    repeating the irradiation step during another rotation along the treatment single arc path(s).

13. The method of claim 10, wherein each set of MLC aperture sequences form a shortest path single arc thereof, said sets connected to form a shortest path treatment single arc.

14. A system for delivering radiation treatment using single arc dose painting, comprising:
    a radiation source for generating a radiation beam;
    a multiple leaf collimator having a plurality of leafs for shaping the radiation beam;
    structure for generating an unconstrained optimization map of intensity profiles of densely-spaced radiation beams;
    structure for aligning each intensity profile to a pair of multiple leaf collimation (MLC) leaves; and
    structure for applying a shortest path algorithm, said shortest path algorithm converting each pair of MLC leaves to a set of leaf aperture sequences forming a shortest path single arc thereof, said shortest path algorithm further connecting each single arc of leaf apertures to form a final treatment single arc effective for single arc dose painting.

15. The system of claim 14, the shortest path algorithm further adjusting a shape of the leaf aperture as a radiation dose delivery angle changes along the final treatment single arc.

16. The system of claim 14, wherein the shortest path algorithm sequences leaf apertures via one or more of a line segment approximation on component intensity profiles leaf position, weight optimization of apertures or optimization of leaf position and aperture weight.

17. The system of claim 14, wherein the multiple leaf collimator is dynamic.

18. A computer-readable medium tangibly storing an algorithm to determine a final single arc path for a single arc dose painting radiation treatment, said algorithm enabling processor-executable instructions to:
    convert pairs of multiple leaf collimation (MLC) leaves to sets of leaf aperture sequences that form a shortest path single arc thereof, said pairs of MLC leaves each aligned to an intensity profile of densely-spaced radiation beams; and
    connect each single arc of leaf apertures to form a final treatment single arc.

19. The computer-readable medium of claim 18, said algorithm further enabling instructions to:
    adjust a shape of the leaf aperture as a radiation dose delivery angle changes along the final treatment single arc.

20. The computer-readable medium of claim 18, wherein the algorithm sequences leaf apertures via one or more of a line segment approximation on component intensity profiles leaf position, weight optimization of apertures or optimization of leaf position and aperture weight.

* * * * *